(12) United States Patent  (10) Patent No.: US 7,824,609 B2
Konertz et al.                (45) Date of Patent: Nov. 2, 2010

(54) METHOD FOR DECELLULARIZING FOREIGN MATERIAL TO PRODUCE BIOPROSTHESES

(75) Inventors: Wolfgang Konertz, Berlin (DE); Pascal Dohmen, Berlin (DE)

(73) Assignee: Auto Tissue GmbH, Berlin (DE)

( * ) Notice: Subject to any disclaimer, the term of this patent is extended or adjusted under 35 U.S.C. 154(b) by 0 days.

(21) Appl. No.: 11/925,618

(22) Filed: Oct. 26, 2007

(65) Prior Publication Data

US 2008/0095662 A1   Apr. 24, 2008

Related U.S. Application Data

(63) Continuation of application No. 10/416,697, filed as application No. PCT/DE01/04616 on Dec. 5, 2001, now abandoned.

(30) Foreign Application Priority Data

Dec. 20, 2000   (DE)   ................. 100 64 948

(51) Int. Cl.
  *A61L 2/00* (2006.01)
  *A61L 2/18* (2006.01)
  *A61L 9/00* (2006.01)
(52) U.S. Cl. ................. 422/28; 422/1; 422/292; 422/300
(58) Field of Classification Search ............... None
  See application file for complete search history.

(56) References Cited

U.S. PATENT DOCUMENTS

| 4,315,919 | A | 2/1982 | Shabrom |
| 4,546,642 | A | 10/1985 | Swanson |
| 4,647,283 | A | 3/1987 | Carpentier et al. |
| 4,782,015 | A | 11/1988 | Allison et al. |
| 4,801,299 | A * | 1/1989 | Brendel et al. ............ 623/1.47 |
| 5,141,847 | A * | 8/1992 | Sugimachi et al. ........... 435/1.2 |
| 5,298,222 | A | 3/1994 | O'Leary |
| 5,308,763 | A | 5/1994 | Ronnett et al. |
| 5,558,875 | A | 9/1996 | Wang |
| 5,846,828 | A * | 12/1998 | Peterson et al. ............ 435/399 |
| 5,993,844 | A | 11/1999 | Abraham et al. |
| 6,258,527 | B1 | 7/2001 | Littman et al. |
| 6,371,992 | B1 | 4/2002 | Tanagho et al. |

(Continued)

FOREIGN PATENT DOCUMENTS

DE   19828726   1/1999

(Continued)

OTHER PUBLICATIONS

English machine translation of JP 06-261933.*

*Primary Examiner*—Elizabeth L. McKane
*Assistant Examiner*—Regina Yoo
(74) *Attorney, Agent, or Firm*—Miles & Stockbridge P.C.

(57) ABSTRACT

The invention relates to a method for decellularising allogenic and xenogenic foreign material for the subsequent production of bioprostheses, coated with endogenous body cells, whereby the foreign material is firstly treated in a solution of bile acid and then alcohol, each with an intermediate or subsequent rinsing step, in combination with a mechanical action on the tissue and the cells by the force generated from a flowing treatment medium, at least in the final rinsing step. After said treatment the tissue is completely rid of foreign cell material and viruses and represents an excellent starting material for the coating with cells of the bioprosthesis recipient.

14 Claims, 3 Drawing Sheets

U.S. PATENT DOCUMENTS

| | | |
|---|---|---|
| 6,376,244 B1 | 4/2002 | Atala |
| 6,482,584 B1 * | 11/2002 | Mills et al. ............. 435/1.1 |
| 6,534,095 B1 | 3/2003 | Moore-Smith et al. |
| 2006/0212074 A1 * | 9/2006 | Umezu et al. ............. 607/1 |

FOREIGN PATENT DOCUMENTS

| | | |
|---|---|---|
| EP | 0564786 | 10/1993 |
| EP | 0989867 | 1/1999 |
| JP | 06261933 A * | 9/1994 |
| JP | 2000198998 | 7/2000 |
| WO | WO 84/01894 | 5/1984 |
| WO | WO 95/24873 | 7/1995 |
| WO | WO 96/32905 | 10/1996 |
| WO | WO 97/18842 | 5/1997 |
| WO | WO 9718842 | 5/1997 |
| WO | WO 99/00152 | 1/1999 |
| WO | WO 01/49210 | 7/2001 |

* cited by examiner

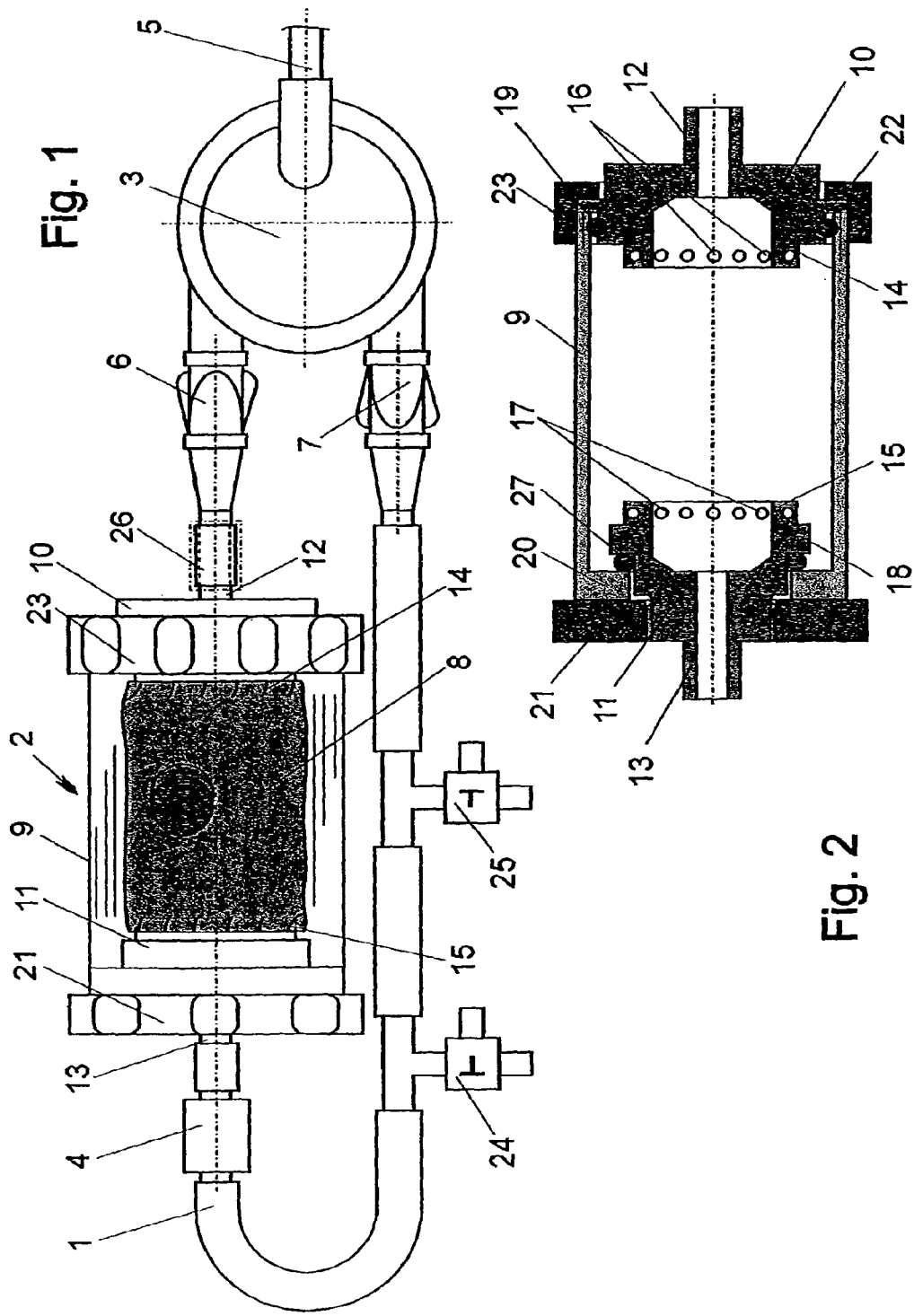

METHOD FOR DECELLULARIZING FOREIGN MATERIAL TO PRODUCE BIOPROSTHESES

CROSS-REFERENCE TO RELATED APPLICATION

This application is a continuation of application Ser. No. 10/416,697 filed Jun. 20, 2003 now abandoned, which is a 371 of International Application No. PCT/DE01/04616 filed Dec. 5, 2001.

The present invention relates to a method for decellularizing allogenic and xenogenic foreign material using biodetergents for the production of bioprostheses coated with endogenic cells of the recipient of the prosthesis.

It is required to provide an "acellular" structure that is free from foreign cells in order to prevent immunological reactions and to ensure the growth and regeneration of the newly established endogenic cells for producing bioprostheses from allogenic and xenogenic foreign material coated with endogenic cells of the later recipient. However the known decellularization methods and uses of biodetergents fail to extract the entire cell material from the tissue matrix so that viral—as yet unknown—effects, e.g. as can be produced by viruses contained in porcine tissue, cannot be excluded.

It is the problem of the present invention to specify a method for decellularizing foreign material intended for being coated with endogenic cells that ensures complete but gentle removal of cells from the foreign tissue.

This problem is solved according to the invention by a method comprising the characteristics described in claim 1.

In other words, the inventive idea is to remove foreign cells from the initial allogenic or xenogenic product to be re-coated with endogenic cells by combining a treatment with bile acid, a treatment with alcohol and upstream and downstream rinsing steps with the mechanical impact of a flowing medium on the tissue matrix and the cells to be removed at least in the last rinsing step.

The bile acid that is preferably used in the form of deoxycholic acid causes gradual—or with a mechanical impact, accelerated—coating of the cells with the acid to create a separating layer between the matrix made of collagen and elastin (hereinafter called 'collagen matrix') and the cell and to detach the cell from the matrix. At the same time, deoxycholic acid has a cytolytic effect. The detached cells and the deoxycholic acid are rinsed off in a subsequent rinsing step. The subsequent treatment with alcohol, preferably with ethanol or propanol, completely disposes of any residual deoxycholic acid as it dissolves well in alcohol. The residual deoxycholic acid that may be present detaches any cells that remained in the matrix while the alcohol has a cytocidal and anti-viral effect. The subsequent last rinsing step is a preferably pulsating flow whose forces act upon the walls of the respective organ portion and expand the matrix but also apply a direct mechanical force onto residual cells and remove them from the expanded matrix.

It is conceivable that other or all steps of the method are connected with such mechanical action by a preferably pulsating flow. Thus the pulsating deoxycholic acid flow mentioned above results in faster formation of the separating layer between the cell and the collagen matrix due to the movement and expansion of the matrix and makes detaching the cell easier due to the forces that act upon it.

The subclaims and the subsequent description of an embodiment disclose other characteristics and advantageous improvements of the invention.

Using the proposed method, it is possible to provide acellular initial products, i.e. organ portions such as cardiac valves or vessels that are free from any cell material and viruses for producing bioprostheses by subsequently coating these products with endogenic cells from their respective recipient.

The apparatus for treating an organ portion consisting of a foreign material in a flowing medium includes a decellularization chamber that receives the respective organ portion and a pump that creates the medium flow, both sequentially incorporated in a ring line. The ring line includes inlet and outlet valves for feeding or draining the respective treatment medium. The decellularization chamber can be detached from the ring line so that said chamber and the organ portion in the medium it contains can be moved. The organ portion to be treated is fixed and preloaded in the container by sewing it to adapters shaped like the organ portion and placing it lengthwise in the direction of flow.

An embodiment of the invention is explained in greater detail below with reference to the figures. Wherein:

FIG. 1 shows an apparatus for decellularizing a cardiac valve in a flow circuit;

FIG. 2 shows a sectional view of the decellularization chamber that is incorporated in the flow circuit and receives the cardiac valve;

FIG. 3b shows a magnified view of a medial tissue section of the aortic valve wall according to FIG. 3a.

Figure 3A:
FIG. 3a shows a microscopic sectional view of an aortic valve wall that has been decellularized using the method according to the invention.
Figure 3B:
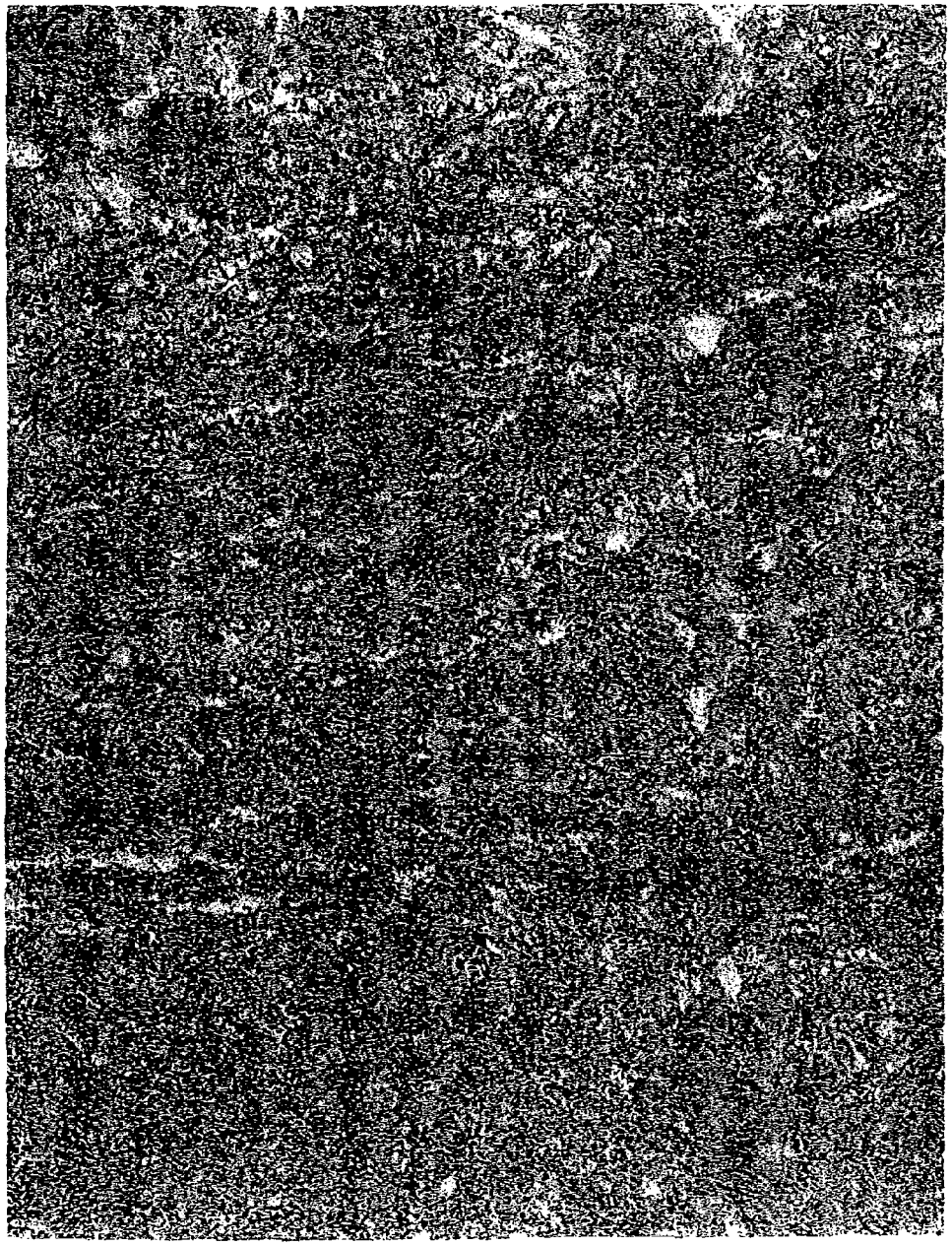

In the embodiment described here, a porcine aortic valve that was removed at a slaughterhouse is freed from fat, cut to size, measured, and checked for germs (fungi, aerobic and anaerobic bacteria, mycoplasma). Intermediate storage at a maximum temperature of 4° C. should not exceed seven days.

The cardiac valve prepared in this way is put into a 1% to 2% deoxycholic acid solution (or a bile acid with a similar effect) and stored therein for 24 hours at 37° C. The deoxycholic acid is capable of forming so-called adducts with a fatty acid in the form of inclusion compounds so that the deoxycholic acid can encompass the cell on all sides, thereby dissolving its adhesive bond with the tissue matrix. At the same time, deoxycholic acid has a cytocidal effect.

Subsequently, a cardiac valve treated in this way is rinsed under constant motion in a dilution set of a phosphate buffer solution (PBS) at decreasing concentrations to remove the cells treated with deoxycholic acid from the tissue matrix.

In a subsequent third step, the cardiac valve is treated at room temperature for about 10 minutes in 40 percent alcohol to produce an antiviral effect and kill any remaining cells in the collagen structure. As alcohol is a good solvent, it at the same times rinses off any residual acid and detaches more cells.

Using another set of a phosphate buffer solution (PBS), the cardiac valve is rinsed once again and then treated mechanically in a pulsating PBS media flow. The pulsating media flow rhythmically widens the cardiac valve that is fixed and preloaded lengthwise to the flow in a decellularization chamber and at the same time exposed to mechanical forces. This step mechanically detaches any remaining cells from the collagen structure so that an acellular structure is obtained from which all cell material has been removed and which therefore cannot contain any viruses. A tissue matrix of the cardiac valve treated in this way which is free of cells and of the decellularization media used—as shown in FIG. 2—is excellently suited for re-coating with endogenic endothelial cells from the later recipient of such a bioprosthesis, and this bioprosthesis can be implanted into a human body without the risk of immunological reactions or viral influences.

The invention is not limited to the treatment variant described herein, both regarding the type and origin of the foreign material used for producing bioprosthesis and regarding the procedural parameters as long as the essential steps of the method, i.e. treatment with an adduct-forming bile acid and alcohol with intermediate or downstream rinsing in combination with exposure of the respective organ portion to a preferably pulsating flow for gentle mechanical action on the tissue, are executed. The method can also be carried out by running not just the last rinsing step but, instead or in addition, by running other or all treatment steps in a flowing medium. This mechanically supports the effect of the respective medium, whereby better, all-area access to the cells is achieved and the cells are easier detached or removed from the expanded collagen matrix due to the action of the pulsating flow.

An apparatus for decellularizing a cardiac valve is shown in FIG. 1. It includes a ring line 1 that incorporates a decellularization chamber 2 that receives the cardiac valve to be treated, a diaphragm pump 3 and a downstream equalizing chamber 4. The diaphragm pump 3 is connected to a drive unit (not shown) via a hose line 5. An outlet valve 6 and an inlet valve 7 whose functions approximately correspond to that of a cardiac valve are integrated into the two connections of the diaphragm pump 3 to the ring line 1. The outlet valve 6 can be omitted when treating cardiac valves as these have valve flaps.

The core of the apparatus is the decellularization chamber 2 for decellularizing a porcine aortic valve 8 using the additional effect of fluid force. The decellularization chamber 2 consists of a transparent hollow cylinder 9 made of piacryl into the open end faces of which the teflon adapters 10 and 11 are sealingly centered and fixed, said adapters being connected to the ring line 1 via fittings 12, 13, each of them comprising a fixing section 14, 15 that protrudes into the hollow cylinder 9 and has mounting holes 16, 17 radially spaced around its periphery for firmly holding the aortic valve 8 in a preloaded state to the rims of the end faces. The outer diameter of the two fixing sections 14, 15 of the adapters 10,11 approximately is the same as the diameter of the aortic valve 8. The rear adapter 11 can be braced via a bridge 18 and a first packing 27 on the inside of a ring land 20 that is connected to the hollow cylinder 9 by turning a threaded ring 21 whose female thread engages in a male thread on the adapter 11. The adapter 10 comprises a collar 22 that rests against the end surface of the hollow cylinder 9 and can be braced using a threaded cap 23 with a female thread that engages in a male thread on the hollow cylinder 9. A second packing 19 is provided for leak proof mounting. The hose piece of the ring line 1 that is topped by the decellularization chamber is made of a flexible material (silicone) to ensure flow-through due to the pulsating pumping effect.

Due to the design and arrangement of the adapters 10, 11 as described above, a suitably prepared aortic valve 8 can be sewed outside the hollow cylinder 9 to the opposite fixing sections 14, 15 of the adapters 10, 11. The aortic valve 8, fixed as described above, is inserted into the hollow cylinder 9. First, the deoxycholic acid is introduced into the decellularization chamber 2 and the ring line 1 via an inlet and outlet valve 24, 25 in the ring line 1 or one of the fittings 13, 14; then, the diaphragm pump 3 is activated so that a pulsating flow of deoxycholic acid continuously flows by or through the aortic valve 8, and the mechanical force this flow exerts on the tissue completes the detachment and removal of cells that are foreign to the recipient of the cardiac valve. Physiological saline or phosphate buffer solution is filled into the apparatus after discharging the deoxycholic acid, and the tissue is rinsed until all the deoxycholic acids and any toxic constituents are removed. After this rinsing step, treatment of the aortic valve 8 with alcohol and another rinsing step in phosphate buffer solution follow.

All treatment steps of the decellularization method take place in the apparatus described above in a pulsating flow of the respective medium. The direction of flow is the natural flow direction when the bioprosthesis is implanted. The inlet and outlet valves 24, 25 are used for media replacement, however fresh rinsing solution can be supplied, and used rinsing solution can be discharged, continuously for the rinsing step.

It is optionally possible to carry out one or several treatment steps disconnected from the ring line and diaphragm pump without any medium flowing through the decellularization chamber, which optionally may be turned manually or using a motor, or, as stated above, to carry out individual treatment steps outside the decellularization chamber.

LIST OF REFERENCE SYMBOLS

1 Ring line
2 Decellularization chamber
3 Blood pump/diaphragm pump
4 Equalizing chamber
5 Hose line (for 3)
6 Outlet valve
7 Inlet valve
8 Aortic valve (bioprosthesis)
9 Hollow cylinder
10 First adapter (front end in the direction of flow)
11 Second adapter (rear end in the direction of flow)
12 Fitting
13 Fitting
14 Fixing section
15 Fixing section
16 Mounting holes
17 Mounting holes
18 Bridge of 11
19 First packing
20 Ring land of 9
21 Threaded ring
22 Collar of 10
23 Male threaded cap
24 Inlet and outlet valve
25 Inlet and outlet valve
26 Diaphragm valve

The invention claimed is:

1. In a method of performing a decellularizing treatment of a cell-containing cardiovascular tissue matrix to prepare a bioprosthesis to be coated with endogenic cells from a recipient of the prosthesis, said cardiovascular tissue being of allogenic or xenogenic origin, the improvement consisting of the following steps:

1) providing a treatment apparatus for circulating a treatment medium in contact with said cardiovascular tissue matrix, said treatment apparatus including:

a treatment chamber having a chamber inlet fitting for a treatment medium and a chamber outlet fitting for said treatment medium;

a holder within said treatment chamber for holding said cardiovascular tissue matrix;

a diaphragm pump having a pump inlet in fluid transmissive communication with said chamber outlet fitting and a pump outlet in fluid transmissive communication with said chamber inlet fitting to circulate said treatment medium through said chamber; and at least one of a pump inlet valve connected to said pump inlet and a pump outlet valve connected to said pump outlet;

2) fixing said cardiovascular tissue matrix to said holder;

3) contacting said cell-containing cardiovascular tissue matrix with a first medium containing a bile acid by circulating said first medium through said treatment chamber;

4) rinsing said cardiovascular tissue matrix with a second medium by circulating said second medium through said treatment chamber;

5) contacting said cardiovascular tissue matrix with a third medium containing alcohol by circulating said third medium through said treatment chamber; and 6) rinsing said cardiovascular tissue matrix with a fourth medium by circulating said fourth medium through said treatment chamber;

each of said media in said steps 4) and 6) being a buffer solution; and said cardiovascular tissue matrix being subjected to mechanical action produced by unidirectional pulsating continuous flow of a respective medium in at least step 6).

2. The improvement of claim 1, wherein each of said media in steps 4) and 6) is a phosphate buffer solution.

3. The improvement of claim 1, wherein said cardiovascular tissue matrix is subjected to mechanical action produced by unidirectional pulsating continuous flow of a respective medium in at least one of said steps 3) to 5).

4. The improvement of claim 3, wherein said cardiovascular tissue matrix is subjected to mechanical action produced by unidirectional pulsating continuous flow of a respective medium in all of said steps 3) to 5).

5. The improvement of claim 1, wherein said cardiovascular tissue matrix is a heart valve.

6. The improvement of claim 1, wherein in said step 3) said first medium is a solution consisting essentially of bile acid and a solvent, and said step 3) is performed at a temperature of about 37° C.

7. The improvement of claim 1, wherein in said step 3) said first medium is a solution consisting essentially of bile acid and a solvent.

8. In a method of performing a decellularizing treatment of a cell-containing cardiovascular tissue matrix to prepare a bioprosthesis to be coated with endogenic cells from a recipient of the prosthesis, said cardiovascular tissue being of allogenic or xenogenic origin, the improvement comprising the steps of:

1) providing a treatment apparatus for circulating a treatment medium in contact with said cardiovascular tissue matrix, said treatment apparatus including:

a treatment chamber having a chamber inlet fitting for a treatment medium and a chamber outlet fitting for said treatment medium;

a holder within said treatment chamber for holding said cardiovascular tissue matrix;

a diaphragm pump having a pump inlet in fluid transmissive communication with said chamber outlet fitting and a pump outlet in fluid transmissive communication with said chamber inlet fitting to circulate said treatment medium through said chamber; and at least one of a pump inlet valve connected to said pump inlet and a pump outlet valve connected to said pump outlet;

2) fixing said cardiovascular tissue matrix to said holder; and performing the following steps 3) to 6) in succession:

3) contacting said cell-containing cardiovascular tissue matrix with a first medium containing a bile acid by circulating said first medium through said treatment chamber;

4) rinsing said cardiovascular tissue matrix with a second medium by circulating said second medium through said treatment chamber;

5) contacting said cardiovascular tissue matrix with a third medium containing alcohol by circulating said third medium through said treatment chamber; and 6) rinsing said cardiovascular tissue matrix with a fourth medium by circulating said fourth medium through said treatment chamber;

each of said media in said steps 4) and 6) being a buffer solution; and said cardiovascular tissue matrix being subjected to mechanical action produced by unidirectional pulsating continuous flow of a respective medium in at least step 6).

9. The improvement of claim 8, wherein each of said media in said steps 4) and 6) is a phosphate buffer solution.

10. The improvement of claim 8, wherein said cardiovascular tissue matrix is subjected to mechanical action produced by unidirectional pulsating continuous flow of a respective medium in at least one of said steps 3) to 5).

11. The improvement of claim 10, wherein said cardiovascular tissue matrix is subjected to mechanical action produced by unidirectional pulsating continuous flow of a respective medium in all of said steps 3) to 5).

12. The improvement of claim 8, wherein said cardiovascular tissue matrix is a heart valve.

13. The improvement of claim 8, wherein in said step 3) said first medium is a solution consisting essentially of bile acid and a solvent, and said step 3) is performed at a temperature of about 37° C.

14. The improvement of claim 8, wherein in said step 3) said first medium is a solution consisting essentially of bile acid and a solvent.

* * * * *